US00PP16561P3

(12) United States Plant Patent
van der Voort

(10) Patent No.: US PP16,561 P3
(45) Date of Patent: May 23, 2006

(54) LILY PLANT NAMED 'DORDOGNE'

(50) Latin Name: *Lilium L. oriental*
Varietal Denomination: Dordogne

(75) Inventor: Cees A. van der Voort, Katwijk (NL)

(73) Assignee: Vletter & Den Haan Beheer B.V., Katwijk (NL)

( * ) Notice: Subject to any disclaimer, the term of this patent is extended or adjusted under 35 U.S.C. 154(b) by 12 days.

(21) Appl. No.: 10/607,272

(22) Filed: Jun. 27, 2003

(65) Prior Publication Data

US 2004/0133957 P1 Jul. 8, 2004

Related U.S. Application Data

(60) Provisional application No. 60/392,029, filed on Jun. 28, 2002.

(51) Int. Cl.
*A01H 5/00* (2006.01)

(52) U.S. Cl. ..... Plt./315

(58) Field of Classification Search ..... Plt./315
See application file for complete search history.

(56) References Cited

FOREIGN PATENT DOCUMENTS

| | | |
|---|---|---|
| AU | 2426 | 3/2004 |
| NL | 18202 | 8/1998 |
| NZ | 1608 | 9/1999 |
| PL | 0 894 | 1/2000 |
| ZA | 20032849 | 3/2003 |

OTHER PUBLICATIONS

'Hits' on UPOV–rom, GTI Jouve Retrieval software Plant Variety Database 2004/02.*
Copy of French PBR Certificate No. 011204 granted Dec. 22, 1998.
Copy of German PBR Certificate No. Liu 00095 granted Apr. 16, 1999.
Copy of Chilean PBR Certificate 31/99 grated Mar. 9, 1999, along with an English language translation.
Copy of Belgium PBR Certificate No. 1649 granted Oct. 14, 2000.

* cited by examiner

*Primary Examiner*—Anne Marie Grunbeg
(74) *Attorney, Agent, or Firm*—Foley & Lardner, LLP

(57) ABSTRACT

A new and distinct cultivar of Lily plant named 'Dordogne' characterized by its large, upright, hot pink flowers with yellow and white center colors, and vigorous growth.

1 Drawing Sheet

Latin name of the genus and species of the plant claimed: *Lilium L. oriental* hybrid.
Variety denomination: Dordogne.

BACKGROUND OF THE INVENTION

The present invention comprises a new and distinct cultivar of lily plant, botanically known as *Lilium L.*, and hereinafter referred to by the cultivar name 'Dordogne'.

'Dordogne' is a product of a planned breeding program which had the objective of creating new lily cultivars having many large upright flowers and vigorous growth habit.

'Dordogne' originated from a hybridization made by the inventor, Cees A. van der Voort, in a controlled breeding program in Rijnsburg, the Netherlands in October, 1994. Both the female and male parents are proprietary unnamed *Lilium L.* cultivars (unpatented).

'Dordogne' was discovered and selected as one flowering plant within the progeny of the stated cross by the inventor in October, 1994 in a controlled environment in Rijnsburg, the Netherlands.

The first act of asexual reproduction of 'Dordogne' was accomplished when scales were taken from the initial selection and grown to maturity in a controlled environment in Rijnsburg, the Netherlands by, or under the supervision of, Cees A. van der Voort. Horticultural examination of selected plants has demonstrated that the combination of characteristics as herein disclosed for 'Dordogne' are firmly fixed and are retained through successive generations of asexual reproduction.

BRIEF DESCRIPTION OF THE INVENTION

The following traits have been repeatedly observed and are determined to be basic characteristics of 'Dordogne' which in combination distinguish this lily as a new and distinct cultivar:

1. large hot pink flowers with yellow and white center colors; and
2. vigorous growth habit.

Of the many commercial cultivars known to the present inventor, the most similar in comparison to 'Dordogne' is the Lily cultivar 'Tiber', described in pending U.S. plant patent application Ser. No. 09/357,097. However, in side-by-side comparisons conducted by the inventor in Stige, Denmark, the main distinctions between the two cultivars are the following characteristics:

1. Plants of 'Dordogne' have firmer stems than 'Tiber'; and
2. Plants of 'Dordogne' have flowers with a more intense red color than 'Tiber'.

'Dordogne' has not been observed under all possible environmental conditions. The phenotype of the new cultivar may vary significantly with variations in environment such as temperature, light intensity, and daylength without any change in genotype.

BRIEF DESCRIPTION OF THE DRAWING

The accompanying color photographic drawing shows a side-view of a typical plant of 'Dordogne', with colors being as true as possible with illustrations of this type. The drawing shows the large hot pink flowers with yellow and white center colors, the buds, and leaves of the plant.

DETAILED BOTANICAL DESCRIPTION

The following observations, measurements and values describe the new cultivar as grown in Rijnsburg, The Netherlands under conditions which closely approximate those generally used in commercial practice. The plant was grown under controlled climate conditions, in greenhouse constructions. Color references are made to The Royal Horticultural Society (R.H.S.) Colour Chart (publication date 2001), except where general colors of ordinary significance are used. Color values were taken under daylight conditions at approximately 12.00 p.m. in Rijnsburg, The Netherlands. The age of the plant described is about 90 days.

Parentage:

*Male parent.*—Unnamed proprietary seedling (unpatented).

*Female parent.*—Unnamed proprietary seedling (unpatented).

Propagation: Scales were taken from the bulbs.

Plant:

General appearance and form:

*Height.*—Medium to tall, 110 cm, depending on growing conditions.

*Flowering season.*—All year round in controlled climate conditions in the greenhouse. Winter hardiness/weather tolerance: None.

*Lastingness of the individual bloom.*—21 days, depending on storing conditions.

*Rooting habit.*—Vigorous.

*Fragrance.*—Strong, typical to lily plants.

Stem description:

*Length.*—Medium to high, 100 cm., depending on growing conditions.

*Diameter.*—3 mm.

*Strength.*—Strong.

Foliage:

*Overall shape of leaf.*—Ovate.

*Quantity.*—Approximately 35–45, depending on growing conditions.

*Length.*—Medium, 11.5 cm, depending on growing conditions.

*Width.*—Medium to wide, 2.5–3 cm, depending on growing conditions.

*Texture.*—Minimal pubescence.

*Color of upper surface.*—Mature leaf: Dark green — RHS 136B. Immature leaf: Medium green — RHS 139C.

*Color of lower surface.*—Mature leaf: Medium green — RHS 136B. Immature leaf: Dark green — RHS 139B.

*Venation color.*—Upper surface: Dark green — RHS 136B (mature leaf); medium green — RHS 139C (immature leaf). Lower surface (mature leaf and immature leaf): Medium green — RHS 136C.

*Petiole.*—Length: 90 mm. Color: Medium green — RHS 136C.

Flowers:

*Flower type and habit.*—Raceme.

*Flower size.*—16 cm in diameter.

*Overall shape.*—Generally hexagonal star in form and bowl-shaped in cross-section.

*Average number of flowers per lateral branch.*—2, depending on growing conditions.

*Tepals.*—Number of tepals: 6. Texture: Papillose. Tepal size: Medium to long in length, 9 cm; medium width, 4 cm. Tepal Color: Upper surface: Purple, RHS 58A, becoming blueish with age. Lower surface: Purple, RHS 58A. Tepal spotting: Present.

Bud:

*Form.*—Tapering.

*Color.*—Yellowish-green — RHS 144C.

*Length.*—8 cm, depending on growing conditions.

*Diameter.*—3 cm, depending on growing conditions.

*Peduncles.*—6 cm length, angle upright, color: medium green — RHS 138B.

Reproductive organs:

*Stamen.*—Number: 6. Color: Yellowish green RHS 144B.

*Seeds.*—None.

*Fruit.*—None.

*Anthers.*—Quantity: 6. Color: Green — RHS 144B.

*Pollen.*—Color: Dark orange red RHS 35A.

*Stigma.*—Quantity: 1. Color: Purple — RHS 75A.

Disease resistance: No known information.

I claim:

1. A new and distinct cultivar of Lily plant named 'Dordogne', as illustrated and described herein.

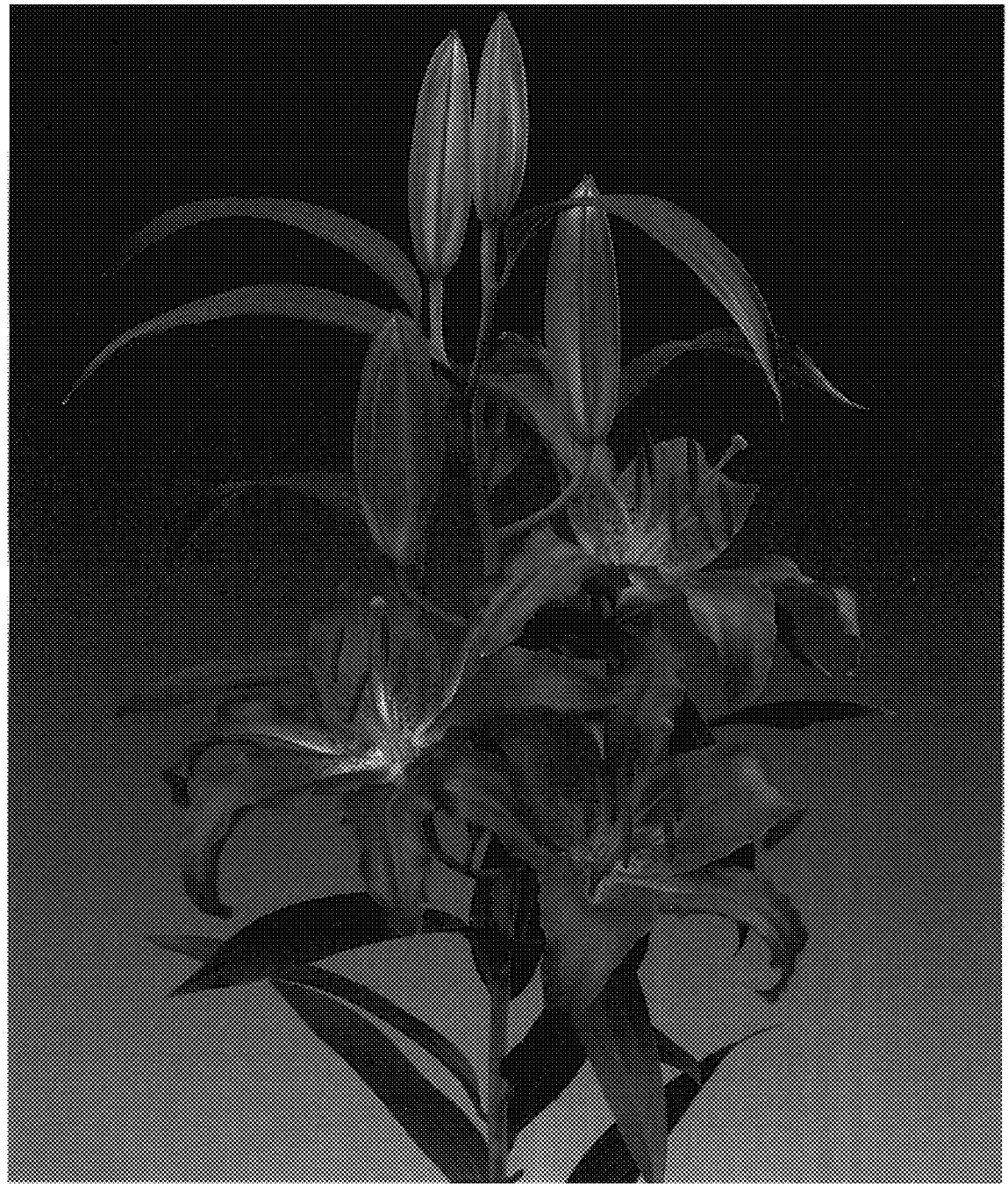

* * * * *